United States Patent [19]

Meanwell

[11] Patent Number: 5,196,428
[45] Date of Patent: Mar. 23, 1993

[54] IMIDAZO[4,5-B]QINOLINYL OXY ALKYL UREAS

[75] Inventor: Nicholas A. Meanwell, East Hampton, Conn.

[73] Assignee: Bristol-Myers Squibb Company, New York, N.Y.

[21] Appl. No.: 862,899

[22] Filed: Apr. 3, 1992

[51] Int. Cl.[5] .............. A61K 31/495; A61K 31/505; A61K 31/535; C07D 401/00

[52] U.S. Cl. .............................. 514/253; 514/232.8; 514/256; 514/293; 544/126; 544/333; 544/361: 546/82

[58] Field of Search ...................... 544/126, 361, 333; 546/82; 514/232.8, 253, 293, 256

[56] References Cited

U.S. PATENT DOCUMENTS

| | | | |
|---|---|---|---|
| 3,932,407 | 1/1976 | Beverung, Jr. et al. | 514/253 |
| 4,256,748 | 3/1981 | Chodnekar et al. | 514/253 |
| 4,490,371 | 12/1984 | Jones et al. | 514/253 |
| 4,668,686 | 5/1987 | Meanwell et al. | 514/253 |
| 4,701,459 | 10/1987 | Meanwell et al. | 514/253 |
| 4,775,674 | 10/1988 | Meanwell et al. | 514/253 |
| 4,943,573 | 7/1990 | Meanwell | 514/253 |

FOREIGN PATENT DOCUMENTS 153152 8/1985 European Pat. Off. .

OTHER PUBLICATIONS

S. Seiler, et al., "Imidazoquinoline Derivatives: Potent Inhibitors of Platelet cAMP Phosphodiesterase which Elevate cAMP Levels and Activate Protein Kinase in Platelets," Throm.Res., 62: 31–42 (1991).

Kozak, et al., Bull. Intern. Acad. Polanaise, 1930A: 432–438 (Chem. Abs. 25, 5400).

J. S. Fleming, et al., New Drugs Annual: Cardiovascular Drugs, Raven Press, 277–294, N.Y. (1983).

J. S. Fleming, J. O. Buchanan, S. M. Seiler, and N. A. Meanwell, "Antithrombotic Acticity of BMY 43351, a New Imidazoquinoline with Enhanced Aqueous Solubility," Thromb.Res., 63, 145–155 (1991).

T. Shioiri, K. Ninomiya and S. Yamada, "Diphenylphosphoryl Azide. A New Convient Reagent for a Modified Curtius Reaction for the Peptide Synthesis," J.Amer.Chem.Soc., 94, 6203–6205 (1972).

M.C. Venuti, et al., "Inhibitors of Cyclic AMP Phosphodiesterase. 2. Structural Variations of N-Cyclohexyl-N-Methyl-4-[(1,2,3,5-tetrahydro-2-oxoimidazo-[2,1-b]quinazolin-7-yl)oxyl]butyramide (RS82856)", J.Med.Chem., 30, 303–318 (1987).

Primary Examiner—Cecilia Tsang

[57] ABSTRACT

A novel series of 1,3-dihydro-2H-imidazo[4,5-b]quinolin-2-ones having enhanced water solubility bioavailability and metabolic stability is disclosed in the Formula I

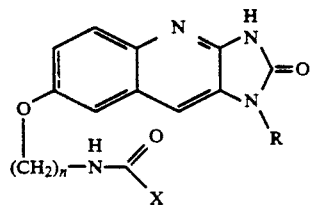

Wherein
R is H, or $C_1$-$C_4$ lower alkyl;
X is $OR^1$, $NR^2R^3$, or

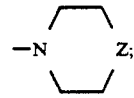

Z is O, NH, $N(CH_2)_mR^5$ or $CHR^6$;
$R^1$ is $C_1$-$C_4$ lower alkyl;
$R^2$ is H, or $C_1$-$C_4$ lower alkyl;
$R^3$ is H, $C_1$-$C_4$ lower alkyl, or $C_4$-$C_8$ cycloalkyl;
$R^5$ is $C_1$-$C_8$ alkyl, $C_4$-$C_8$ cycloalkyl, 2-pyranyl, 2-thienyl, 3-thienyl, piperidinyl-N-CH, N-2-pyridyl, N-2-pyrimidinyl, or substituted or unsubstituted phenyl wherein the substituent is halogen;
$R^6$ is H, 1-piperidinyl, or phenylmethyl;
m is an integer of 1-3; and
n is an integer of 1-5;

or pharmaceutically acceptable salt thereof.

The compounds are useful as inhibitors of ADP-induced blood platelet aggregation in human platelet-rich plasm.

22 Claims, No Drawings

IMIDAZO[4,5-B]QINOLINYL OXY ALKYL UREAS

BACKGROUND OF THE INVENTION

1. Field of the Invention

This invention relates to a new class of selective and potent inhibitors of platelet cyclic AMP phosphodiesterase. In particular, the invention relates to a series of new carboxamido derivatives of imidazo[4,5-b]quinolin-2-one which are useful as inhibitors of ADP-induced aggregation of human blood plateletes in platelet-rich plasma.

2. Description of the Art

Platelet aggregation is considered part of a complex physiological mechanism for formation of a thrombus in the vascular system. Thromboembolic phenomena, i.e., the formation of thrombi, are involved in hemostasis and a number of diseased states in mammals including thrombophlebitis, phlebothrombosis, cerebral thrombosis, coronary thrombosis and retinal vessel thrombosis. An increase in propensity for platelet aggregation, sometimes referred to as platelet adhesiveness, is observed following parturition, surgical operations such as coronary artery bypass surgery, organ transplant, angioplasty, prosthetic heart valve implants to name a few; and in ischemic heart disease, atherosclerosis, multiple sclerosis, intracranial tumors, thromboembolism, and hyperlipemia (A. Poplawski, et al, *J. Atherosclerosis Research.* 8: 721 (1968)).

The imidazo[4,5-b]quinolin-2-one derivatives have been identified as potent inhibitors of human blood platelet cAMP phosphodiesterase (PDE) and in vitro aggregation induced by ADP and collagen (Seiler et al., *Thromb. Res.,* 62, 31–42 (1991).

The heterocycle "2,3-dihydro-2-oxo-1H-imidazo[4,5-b]quinoline" of the formula (1), alternately referred to as 1,3-dihydro-2H-imidazo[4,5-b]quinolin-2-one, was described by Kozak, et al, *Bull. Intern. Acad. Polanaise,* 1930A, 432–438 (Chem. Abs. 25, 5400)

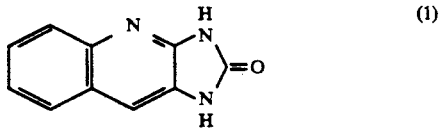

Derivatives of formula (1) having cyclic AMP phosphodiesterase inhibitory activity have been prepared and studied for their platelet inhibition and cardiotonic properties. Thus, for example:

Meanwell, N. A., U.S. Pat. No. 4,943,573 describes a series of 2,3-dihydro-2-oxo-1H-imidazo-[4,5-b]quinolin-2-ones comprising derivative of the formula (2)

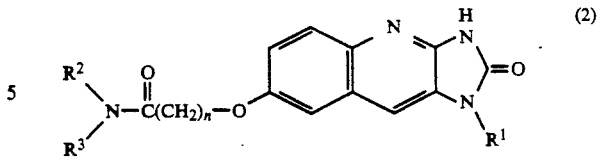

wherein n is 3 to 5; $R^1$ is hydrogen or alkyl of 1 to 4 carbon atoms; $R^2$ is hydrogen; $R^3$ is 1-piperidinylethyl, 1-benzylpiperidin-4-yl, 4-(1-piperidinyl)piperidine, (1-alkyl-2-pyrrolidinyl)alkyl where alkyl is 1 to 4 carbon atoms, 3-quinuclidinyl; $R^2$ and $R^3$ together with the nitrogen atom to which they are attached form 4-$R^4$-piperazin-1-yl wherein $R^4$ is alkyl of i to 7 carbon atoms, alkoxyethyl of 3 to 7 carbon atoms, pyridinyl, pyrimidinyl, tetrahydropyranylmethyl, thienylmethyl, cycloalkyl-$(CH_2)_m$ where m is zero or one and cycloalkyl is 5 to 7 carbon atoms except m is zero when cycloalkyl is 7 carbon atoms, benzyl, 4-fluorobenzyl, 3-trifluoromethylbenzyl, 4-alkoxybenzyl where alkoxy is 1 to 4 carbon atoms.

Among the compounds disclosed is the compound of the formula (3), identified as 1-(cyclohexylmethyl)-4-(2,3-dihydro-2-oxo-1H-imidazo[4,5-b]quinolin-7-yloxy)1-oxybutyl]piperazine.

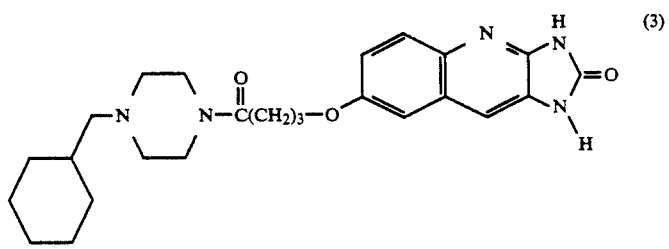

Meanwell, et al. U.S. Pat. No. 4,775,674 describe a series of 2,3-dihydro-2-oxo-1H-imidazo[4,5-b]quinolinyl ether derivatives of the formula (4)

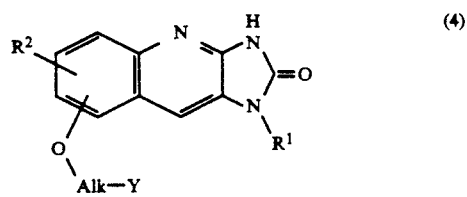

wherein $R^1$ is hydrogen, lower alkyl, benzyl; $R^2$ is hydrogen, halogen, lower alkyl, lower alkoxy; Alk is alkylene; Y is hydroxy and alkanoic or aralkanoic esters thereof, oxo ketone, dialkylamino carboxylic acid and esters, carboxamides, alkoxy, ethanolamines and cyclic carbamates thereof, tetrazoyl, and optionally substituted phenylsulfonyl.

Among the compounds disclosed is the compound of formula (5), identified in the art as 7-[4-(phenylsulfonyl)butoxyl]-1,3-dihydro-2H-imidazo[4,5-b]quinolin-2-one.

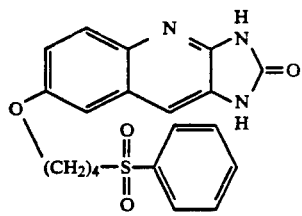

Meanwell, et al, U.S. Pat. No. 4,701,459 describe another series of 2,3-dihydro-2-oxo-1H-imidazo-[4,5-b]quinoline compounds comprising amine derivatives of formula (6)

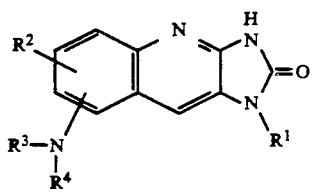

wherein $R^1$ is hydrogen, lower alkyl; $R^2$ is hydrogen, lower alkyl, lower alkoxy, halogen; $R^3$ is hydrogen, lower alkyl; $R^4$ is hydrogen, lower alkyl, alkanoyl, phenylalkanoyl wherein phenyl is optionally substituted with halogen, lower alkyl, lower alkoxy, $R^3$ and $R^4$ are joined together to form morpholinyl, piperidinyl or pyrrolidinyl optionally substituted with —$CO_2R^5$ or

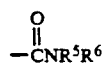

wherein $R^5$ is hydrogen or lower alkyl, and $R^6$ is hydrogen, lower alkyl, cycloalkyl; 4-$R^7$-piperazinyl wherein $R^7$ is —$CO_2R^8$ wherein $R^8$ is lower alkyl, phenyl optionally substituted with up to 2 halogen, lower alkyl or lower alkoxy: phenylalkanoyl of 7 to 10 carbon wherein phenyl is unsubstituted or independently substituted with up to 2 halogen, lower alkyl, lower alkoxy.

Meanwell, et al. U.S. Pat. No. 4,668,686 describe still another series of 1,3-dihydro-2H-imidazo-[4,5-b]quninolin-2-ones comprising derivatives of formula (7)

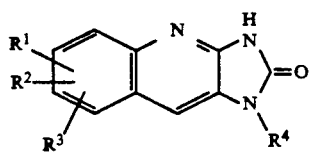

wherein $R^1$ is halogen, lower alkyl, lower alkoxy, trifluoromethyl; $R^2$ is hydrogen, halogen, lower alkyl, lower alkoxy; $R^3$ is hydrogen, halogen, lower alkyl, lower alkoxy; and $R^4$ is hydrogen or lower alkyl.

Another class of heterocyclic compounds having phosphodiesterase inhibiting and anti-platelet aggregation activity comprise the tetrahydroimidazo[2,1-b]quinazolin-2-ones of formula (8)

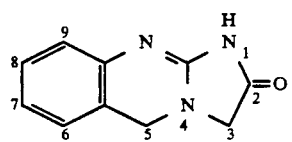

For example:

Beverung, Jr., et al, U.S. Pat. No. 3,932,407 disclose a series of compounds useful as blood platelet antiaggregative and/or antihypertensive and/or bronchodilator agents of tetrahydroimidazo[2,1-b]-quinazolin-2-one class. Anagrelide (9), a particularly preferred member of the Beverung, Jr., et al. series, has been studied extensively, e.g., J. S. Fleming, et al, New Drugs Annual: Cardiovascular Drugs, Raven Press, 277-294, NY (1983).

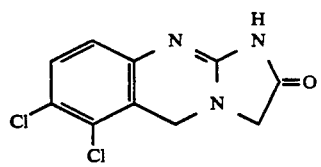

Chodnekar, et al. U.S. Pat. No. 4,256,748 describe a series of tetrahydroimidazo[2,1-b]quinazolin-2-ones of the formula (10) as inhibitors of the aggregation of blood platelets and cardiotonic activity.

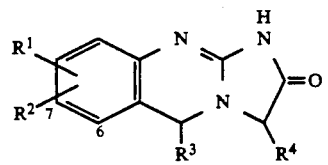

Representative of the Chodneker compounds are RO 15—2041 ($R^4$=$CH_3$, $R^3$=H, $R^2$=6—$CH_3$, $R^1$=7—Br) and RO 13—6438 ($R^4$=$CH_3$, $R^3$=H, $R^2$=6—$CH_3$, $R^1$=H).

Jones, et al, U.S. Pat. No. 4,490,371 describe another series of tetrahydroimidazo[2,1-b]quinazolin-2-one derivatives as cyclic AMP phosphodiesterase inhibitors useful as thrombogenic agents. Among the compounds disclosed is the formula (11) amide, identified in the art as lixazinone.

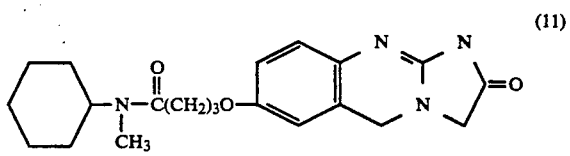

Jones, et al, European Patent Application 153152 further describe tetrahydroimidazo[2,1-b]quinazoline-ones of formula (11) as cyclic AMP phosphodiesterase inhibitors useful as antithrombogenic agents.

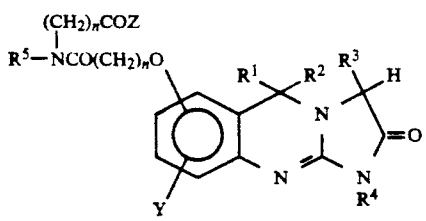

(12)

Compounds of the aforementioned patents generally display limited solubility in water, acidic or alkali media and common organic solvents.

SUMMARY OF THE INVENTION

The present invention provides novel carboxamido derivatives of imidazo [4,5-b]quinolin-2-one derivatives which have enhanced potency and aqueous solubitily.

In particular, the invention relates to a series of 7-oxypropylcarboxamido-imidazo[4,5-b]quinolin-2-ones wherein a urea functionality is incorporated in the side chain terminus. The incorporation of a basic nitrogen atom in the side chain terminus provides compounds that combine a high level of biological activity with good aqueous solubility compared to, for example, the formula (2)–(5), (7), (9), (11) and (12) compounds.

Formula I illustrates the compounds of the invention and the ring numbering system used herein.

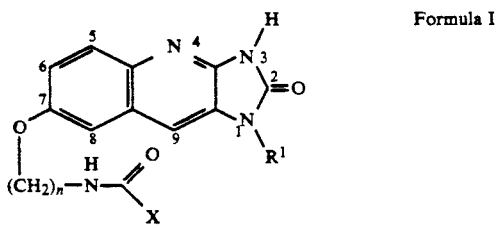

Formula I

In the foregoing Formula I, n, R and X are as described below.

The compounds of Formula I are useful as inhibitors of adenosine diphosphate-induced aggregation of human blood platelets in platelet rich plasma.

The compounds of Formula I have antithrombogenic and phosphodiesterase inhibition properties and are useful in prevention or treatment of conditions involving platelet aggregation and thrombosis.

The compounds of Formula I are also considered to have antimetastatic potential in view of their platelet inhibition properties.

Another embodiment of the invention concerns pharmaceutical compositions comprised of a Formula I compound combined with at least one pharmaceutically acceptable carrier.

Yet another embodiment relates to a method for inhibiting blood platelet aggregation in a mammal which comprises administering a therapeutically effective amount of a compound of Formula I to a mammal in need of such treatment.

DETAILED DESCRIPTION OF THE INVENTION

The compounds of the instant invention comprise those of Formula I.

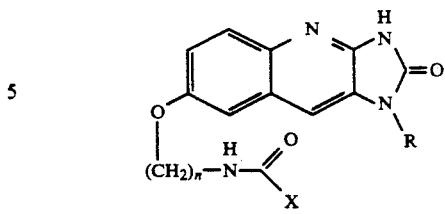

I wherein
R is H, or $C_1$-$C_4$ lower alkyl;
X is $OR^1$, $NR^2R^3$, or

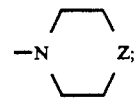

$Z$ is O, NH, $N(CH_2)_mR^5$ or $CHR^6$;
$R^1$ is $C_1$-$C_4$ lower alkyl;
$R^2$ is H, or $C_1$-$C_4$ lower alkyl;
$R^3$ is H, $C_1$-$C_4$ lower alkyl, or $C_4$-$C_8$ cycloalkyl;
$R^5$ is $C_1$-$C_8$ alkyl, $C_4$-$C_8$ cycloalkyl, 2-pyranyl, 2-thienyl, 3-thienyl, piperidinyl-N-CH, N-2
$R^5$ is $C_1$-$C_8$ alkyl, $C_4$-$C_8$ cycloalkyl, 2-pyranyl, 2-thienyl, 3-thienyl, piperidinyl-N—CH, N-2-pyridyl, N-2-pyrimidinyl, or substitued or unsubstituted phenyl wherein the substituent is halogen;
$R^6$ is H, 1-piperidinyl, or phenylmethyl;
m is an integer of 1-3; and
n is an integer of 1-5;
or pharmaceutically acceptable salt thereof.

It is understood that as used herein limitation of Formula I are defined as follows:

The term "halogen" comprehends fluorine, iodine, bromine and chlorine, preferably fluorine and chlorine.

The term "$C_1$-$C_8$ alkyl" refers to a branched or unbranched saturated hydrocarbon chain containing from 1 to 8 carbon atoms, for example, methyl, ethyl, n-propyl, isopropyl, butyl, isobutyl, 3-pentyl, and 4-heptyl.

The term "$C_1$-$C_4$ lower alkyl" refers to a branched or unbranched saturated hydrocarbon chain containing from 1 to 4 carbon atoms, for example, methyl, ethyl, n-propyl, isopropyl, butyl, and isobutyl.

The term "$C_4$-$C_8$ cycloalkyl" comprehends a saturated aliphatic ring containing the designated number of carbon atoms. Such radicals are, for example, cyclobutyl, cyclopentyl, cyclohexyl, cycloheptyl, cyclooctyl.

According to the present invention, two synthetic routes (Method A and Method B) were employed to prepare the compounds characterized by Formula I and the pharmaceutically acceptable acid addition salts thereof.

Method A depicted in Scheme 1, involves installation of the urea functionality early in the nitrobenzaldehyde (1), using diphenylphosphoryl azide (DPPA) (Shioiri et al., *J. Amer. Chem. Soc.* 94, 6203–6205 (1972)) and triethylamine ($Et_3N$) in toluene afforded the isocyanate which was intercepted with ethyl alcohol (EtOH) or an amine to give the corresponding carbamate or urea (5). Deprotection of the aldehyde followed by coupling with diethyl 2,4-dioxoimidazo-lidine-5-phosphonate (Meanwell, et al., *J. Org. Chem.*, 56: 6897–6904 (1991)) afforded the olefin 6 as a mixture of geometrical isomers. The imidazo[4,5-b]quinolin-2-one skeleton was constructed as previously described (U.S. Pat. No.

4,775,674 to Meanwell et al.) and proceeded via exhaustive catalytic hydrogenation over 10% palladium on active carbon (Pd-C) followed by cyclization and concomitant oxidation using $I_2$ in methyl alcohol (MeOH) to provide the target compounds.

Heating a suspension of 8 in dimethylformaldehyde (DMF) containing a 1.5- fold excess of DPPA (Shiori, et al., *J. Amer. Chem. Soc.*, 94: 6203-6205 (1972)) and $Et_3N$ resulted in solution occurring at about 60° C. followed by the formation of a heavy precipitate as the temperature continued to rise. After about 1 hour at about 120° C., the mixture was cooled, diluted with water and a grey solid filtered off. The material isolated in this fashion proved to be extremely insoluble and has not been identified. The IR spectrum, as a KBr disc, shows no absorption in the 2200-2300 $cm^{-1}$ region, indicating the absence of an isocyanate, and shows a single absorption peak at 1750 $cm^{-1}$. Heating a concentrated slurry of the solid in dimethylsulfoxide (DMSO) or 1-methyl-2-pyrrolidinone (NMP) with an excess of a piperazine gave the target compound. This procedure (method B) is shown in scheme 2.

The compounds synthesized as part of this study are listed in Table 1 along with relevant physical data.

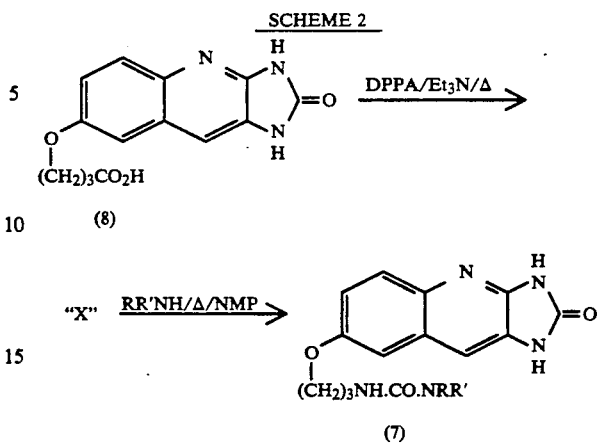

In Vitro Inhibition of Human Platelet Aggregation

The aggregometer method of Born, G. V. R., *J. Physiol.*, (London), 162, 67-68, (1962) as modified by Mustard, J. F., et al., *J. Lab. Clin. Med.*, 64, 548-599, (1964) was used to assess the in vitro activity of the various compounds as to the inhibition of adenosine diphosphate (ADP) and collagen-induced platelet aggregation. The human volunteer donor's arm is cleansed with 70% ethyl alcohol. A sterile 20 ml syringe and needle are used to withdraw 20 ml of blood. The blood is immediately added to a test tube contain-

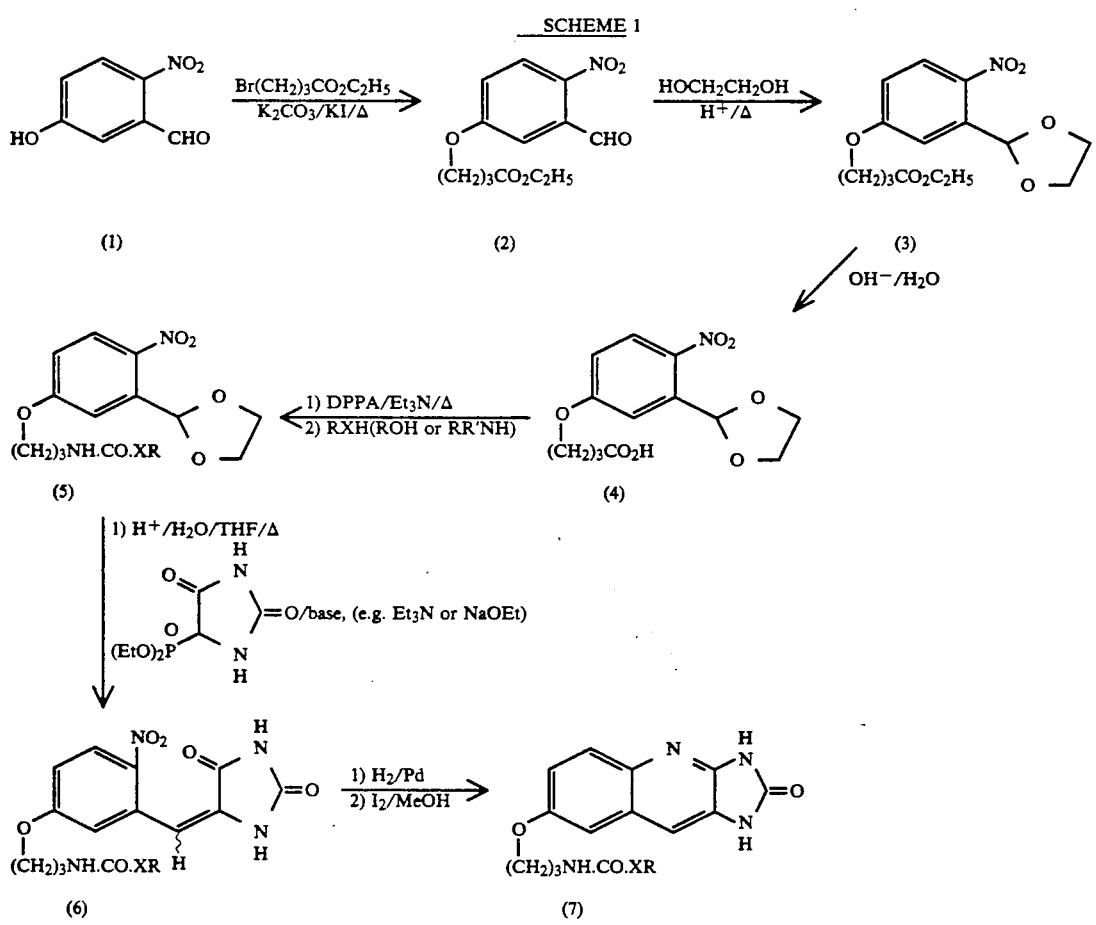

ing 3.8% sodium citrate to prevent clotting (1 part citrate to 9 parts blood).

Platelet rich plasma (PRP) was separated by centrifugation for 10 minutes at 1000 rpm (140 g) from citrated (3.8%) human blood. All glassware used for preparation of PRP is silicon treated. ADP in final concentration of 0.5 mcg/mL or 0.05 mL of a collagen suspension prepared according to the method described by Evans, G., et al., *J. Exp. Med.*, 128, 877–894, (1968) was used to induce aggregation. The various compounds tested were dissolved in dimethylsulfoxide (DMSO) so that 5 mcl added to the platelet rich plasma would yield the desired test concentration. Vehicle control trials were done and compared with aggregation induced in platelet rich plasma containing various concentrations of the test compounds. Dose response curves were obtained and Inhibitor Concentration ($IC_{50}$) values calculated. In this test, the $IC_{50}$ values for dipyridamole, a clinically useful antithrombogenic agent, are 512 mcg/ml vs. ADP and 245 mcg/ml vs collagen. Results for 50% inhibition of ADP-induced aggregation are given hereinafter.

The target compounds were evaluated as inhibitors of ADP-induced aggregation of human blood platelets in platelet-rich-plasma (PRP) in vitro. The standard protocol entailed incubation of drug with PRP for about 3 minutes prior to addition of the agonist and under these conditions the formula (3) compound provided 50% inhibition at a concentration of 0.182 µg/mL. When PRP was incubated with the formulas (3) compound for about 15 minutes prior to adding ADP, the observed $IC_{50}$ was 0.041 µg/mL.

TABLE 1

| Inhibition of ADP-induced Human Platelet Aggregation and Aqueous Solubility by Test Compounds | | |
|---|---|---|
| Cmpd # | $IC_{50}$ vs ADP in human PRP, µg/mL | Aqueous solubility mg/mL |
| 7a | 0.035 | <10 |
| 7b | 0.04 | <10 |
| 7c | 0.3 | <10 |
| 7d | 1.2 | <10 |
| 7e | 0.08 | <0.2 |
| 7f | 0.04 | >20 |
| 7g | 0.03 | 2 |
| 7h | 0.05 | 0.7 |
| 7i | 0.04 | 0.5 |
| 7j | 0.09 | >20 |
| 7k | 0.09 | >20 |
| 7l | 0.022 | >20 |
| 7m | 0.07 | 0.5 |
| 7n | 3.8 | <0.5 |
| 7o | 0.18 | >20 |
| 7p | 0.17 | 0.2 |
| 7q | 0.205 | >20 |
| 7r | 0.17 | 0.25 |
| 7s | 0.09 | >10 |
| 7t | 0.15 | 3 |
| 7u | 5.2 | >20 |
| 7v | 0.17 | 0.1 |
| 7w | 0.38 | 0.5 |

The compounds of Formula I or pharmaceutically acceptable salts thereof have pharmacological properties which make them particularly useful as inhibitors of ADP-induced aggregation of human blood platelets in platelet rich plasma.

Another embodiment of the invention concerns pharmaceutical compositions comprised of a Formula I compound combined with at least one pharmaceutically acceptable excipient.

Yet another embodiment relates to a method for inhibiting blood platelet aggregation in a mammal which comprises administering a therapeutically effective amount of a compound of Formula I to a mammal in need of such treatment.

The dosage employed in the instant therapeutic methods will vary with the form of administration, the particular compound chosen, the subject being tested and the effect desired. Suitable effective doses in animals range from 0.01 to 50 mg/Kg body weight orally and from 0.001 to 20 mg/kg body weight parenterally (generally characterized as subcutaneous, intramuscular, and intravenous injection). It is contemplated that the effective unit dose in man will range from 0.1 to 50 mg/Kg and preferably from 0.5 to 30 mg/Kg administered one to three times a day. In accordance with conventional clinical practice, the effective dose can be determined by administering a Formula I compound at a dosage substantially less than the does of the compound which is thought to be effective and then increasing the dosage in small increments until the desired effect is achieved.

In carrying out the instant therapeutic methods, the active ingredient of Formula I and pharmaceutically acceptable acid addition salts thereof are preferably administered with a pharmaceutically acceptable carrier and such compositions constitute part of the instant invention. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutical acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated by known techniques to delay disintegration and absorption in the gastrointestinal tract and thereby provide a sustained action over a longer period. Similarly, suspension, syrups and elixirs may contain the active ingredient in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl-p-hydroxybenzoate. Capsules may contain the active ingredient alone or admixed with an inert solid diluent such as calcium carbonate, calcium phosphate and kaolin. The injectable compositions are formulated as known in the art and may contain appropriate dispersing or wetting agents and suspending agents identical or similar to those mentioned above.

All publications cited in this specification are indicative of the level of skill of those skilled in the art to which this invention pertains. Each publication is individually incorporated herein by reference in the location where it is cited.

The compounds which constitute the invention and their methods of preparation will appear more fully from a consideration of the following examples. The compounds which are not shown by specific example are readily prepared by analogous procedure. The following examples are given by way of illustration and are not to be construed as limiting the invention in any way inasmuch as many variations of the invention are possible within the spirit of the invention.

All temperatures are degrees Centrigrade and melting points taken with a Thomas Hoover capillary apparatus are uncorrected. Conventional abbreviations are employed in reporting Nuclear Magnetic Resonance (NMR) spectral data with tetramethylsilane as internal reference and chemical shift data values in parts per million.

EXAMPLE 1

N-Cyclohexyl-N'-[3-(3-formyl-4-nitrophenoxy)propyl] urea

4-[3-(1,3-Dioxolan-2-yl)-4-nitrophenoxy]butanoic acid (7.8 g, 26 mmol) was dissolved in $C_6H_6$ (80 mL) with warming at about 45° C. The solution was cooled in an ice bath and $Et_3N$ (2.94 g, 4.1 mL, 29 mmol) and DPPA (8.00 g, 7.1 mL, 29 mmol) added. The mixture was stirred at room temperature overnight and at reflux for about 4 hours before being cooled to room temperature. Cyclohexylamine (2.86 g, 3.3 mL, 29 mmol) was added and the mixture heated at reflux for about 18 hours. The mixture was cooled and concentrated, the residue dissolved in dichloromethane ($CH_2Cl_2$) (400 mL) with warming and washed with water (2×200 mL), 10% sodium carbonate ($Na_2CO_3$) solution (2×200 mL), 50% $NH_4Cl$ solution (200 mL) and brine (200 mL). The organic phase was dried over magnesium sulfate ($MgSO_4$) and the solvent evaporated to leave a waxy solid to which was added tetrahydrofuran (THF) (300 mL) and 2N HCl solution (80 mL). The mixture was heated at reflux for about 2.5 hours, cooled, concentrated and the residue partitioned between $CH_2Cl_2$ (400 mL) and water (200 mL). The organic phase was separated, washed with saturated sodium bicarbonate ($NaHCO_3$) solution (2×200 mL) and water (200 mL), dried over $MgSO_4$ and the solvent evaporated to leave a solid (8.82 g, 86%). A 1.00 g sample was recrystallized from aqueous EtOH to give N-Cyclohexyl-N'-[3-(3-formyl-4-nitrophenoxy) propyl]urea as a yellow solid, mp 150°-152° C. IR (KBr) 1695, 1625, 1575, 1520 cm$^{-1}$; $^1$H NMR (DMSO-d$_6$) δ 0.95–1.95 (12H, m, CH$_2$), 3.17 (2H, q, J=6 Hz, NCH$_2$), 3.38 (1H, bs, NCH), 4.18 (2H, t, J=6 Hz, OCH$_2$), 5.70 (1H, d, J=9 Hz, NH.CO), 5.85 (1H, t, J=6 Hz, NH.CO), 7.24 (1H, d, J=3 Hz, aryl H ortho to CHO), 7.34 (1H, dd, J=9 Hz, J'=3 Hz, aryl H meta to CHO), 8.17 (1H, d, J=9 Hz, aryl H ortho to NO$_2$), 10.30 (1H, s, CHO); MS m/z 350 (MH+).

Anal. Calcd. for $C_{17}H_{23}N_3O_5$:
C, 58.44; H, 6.64; N, 12.03.
Found: C, 58.43; H, 6.64; N, 12.02.

EXAMPLE 2

(E) and (Z)-N-Cyclohexyl-N'-[3-[4-nitro-3-[(2,4-dioxoimidazolidin-5-ylidene)methyl]phenoxy] propyl]urea Sodium (0.50 g, 20 mg atom) was dissolved in absolute EtOH (100 mL), diethyl 2,4-dioxoimidazolidine-5-phosphonate (4.70 g, 20 mmol) added and the mixture stirred at room temperature for about 15 minutes. N-Cyclohexyl-N'-[3-(3-formyl-4-nitrophenoxy)propyl]urea (5.33 g, 15 mmol) in EtOH (75 mL) was added and the mixture stirred for about 1 hour. The solution was acidifed with 2N HCl solution, concentrated to ca. 75 mL and diluted with water. After stirring overnight, a pale yellow solid was filtered off and dried in air to give N-cyclohexyl-N'-[3-[4-nitro-3-[(2,4-dioxoimidazolidin-5-ylidene)-methyl]phenoxy] propyl]urea (6.50 g, 99 %). A 1.00 g sample was recrystallized from aqueous acetonitrile to give 0.79 g as a 5:1 (Z) to (E) mixture, mp 132°-138° C. IR (KBr) 1760, 1725, 1650, 1570, 1500, 1375, 1340, 1290, 1250 cm$^{-1}$; $^1$H NMR (DMSO-d$_6$) δ 1.00 to 2.00 (10H, m, CH$_2$ of cyclohexyl ring), 3.30 (2H, quintet, J=6 Hz, CO.NH.CH$_2$), 3.35 (1H, m, N-CH), 4.11 (0.32H, t, J=6Hz, OCH$_2$ of (Z) isomer), 4.20 (1.67H, t, J=6 Hz, OCH$_2$ of (E) isomer), 6.62 (0.16H, s, olefinic H of (Z) isomer), 6.74 (0.84H, s, olefinic H of (E) isomer), 7.05 to 7.20 (2H, m, aryl H), 8.15 (1H, 2×d, aryl H ortho to NO$_2$); MS m/Z 432 (MH+).

Anal. Calcd. for $C_{20}H_{25}N_5O_6 \cdot 0.3H_2O$:
C, 54.99; H, 5.91; N, 16.03; H$_2$O, 1.24.
Found: C, 55.16; H, 5.96; N, 15.93; H$_2$O, 1.25.

EXAMPLE 3

N-Cyclohexyl-N'-[3-[(2,3-dihydro-2-oxo-1H-imidazo[4,5-b]quinolin-7-yl)oxy]propyl]urea hydrochloride (7c)

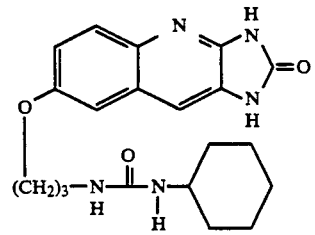

A solution of (E) and (Z)-N-cyclohexyl-N'-[3-[4-nitro-3-[(2,4-dioxoimidazolidin-5-ylidene)-methyl]p henoxy]propyl]urea (5.50 g, 13 mmol) in DMF (100 mL) was hydrogenated over 10% Pd on C (0.60 g) at 60 psi in a Parr hydrogenation apparatus. After hydrogen uptake had ceased, the mixture was filtered through Celite and the DMF removed in vacuo. The residue was dissolved in MeOH (175 mL), a catalytic amount of pTsOH added and the mixture heated at reflux. After about 2 hours, I$_2$ (3.25 g, 13 mmol) was added portionwise over about 5 minutes and the mixture heated at reflux for about 1 hour before cooling to room temperature. A 10% solution of sodium thiosulfate (Na$_2$S$_2$O$_3$) (35 mL) and 10% Na$_2$CO$_3$ solution (7 mL) was added, the mixture concentrated to remove most of the MeOH and diluted with water. A solid was filtered off and dried in air to give 4.47 g. This was dissolved in hot MeOH by addition of an excess of a 10% solution of HCl in MeOH. After filtering, diisopropyl ether was added to precipitate N-cyclohexyl-N'-[3-[(2,3-dihydro-2-oxo-1H-imidazo[4,5-b]quinolin-7-yl)oxy]propyl]urea hydrochloride, (4.52 g, 84%), mp 215°-217° C. (dec.) IR (KBr) 1750 cm$^{-1}$;; $^1$H NMR (DMSO-d$_6$) δ 1.05 to 1.85 (10H, m, CH$_2$ of ring), 1.90 (2H, t, J=6 Hz, CH$_2$CH$_2$O), 3.24 (2H, t, J=6 Hz, CO.NH.CH$_2$), 3.42 (1H, m, CO.NH.CH), 4.11 (2H, t, J=6 Hz, OCH$_2$), 7.32 (1H, dd, J=9 Hz, J'=2 Hz, aryl H ortho to O), 7.52 (1H, d, J=2 Hz, aryl H ortho to O), 7.89 (1H, s, aryl H ortho to CO.NH), 7.99 (1H, d, J=9 Hz, aryl H meta to O); MS m/z 384 (MH+).

Anal. Calcd. for $C_{20}H_{25}N_5O_3 \cdot 1.8HCl \cdot 0.2H_2O$:
C, 53.07; H, 6.06; N, 15.47; Cl, 14.10; H$_2$O, 0.80.
Found: C, 52.94; H, 5.99; N, 15.44; Cl, 14.05; H$_2$O, 0.70.

EXAMPLE 4

N-[3-(2,3-dihydro-2-oxo-1H-imidazo[4,5-b]quinolin-7yloxy)propyl]-4-(2-ethylbutyl)-1-piperazinecarboxamide dihydrochloride (7l)

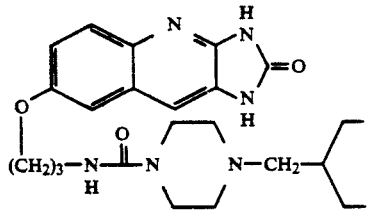

A mixture of 4-[(2,3-dihydro-2-oxo-1H-imidazo [4,5-b]quinolin-7-yl)oxy]butyric acid (11.70 g, 38 mmol), Et₃N (5.37 g, 7.36 mL, 53 mmol), DPPA (14.58 g, 11.50 mL, 53 mmol) and DMF (225 mL) was heated to about 130° C. with stirring. At ca. 50°–60° C., solution occurred followed by the formation of a grey precipitate as the temperature climbed through 100° C. After about 2 hours, the suspension was cooled, diluted with water and a grey solid filtered off, washed with water, MeOH and isobutyl alcohol (Et₂O) to leave 10.65 g.

A slurry of 2 g of this material, 2-ethylbutyl-1-piperazine (2.40 g, 14 mmol) and NMP (4 mL) was heated at about 200° C. for about 30 minutes. The cooled reaction mixture was filtered, the solid washed with DMF (ca. 75 mL) and the filtrate concentrated in vacuo to ca. 30 mL. The solution was diluted with H₂O (45 mL) and the precipitate filtered off and dried in air. The solid material was dissolved in EtOH by the addition of excess of a 10% solution of HCl in EtOH, the mixture heated at reflux for about 30 minutes and cooled to room temperature. Filtration provided a solid (2.32 g, 72%) which was stirred with aqueous Na₂CO₃ solution, filtered and the solid disolved in hot DMF, filtered and diluted with water. The precipitated solid was disolved in EtOH containing an excess of dry HCl gas and diluted with ether to give N-[3-(2,3- dihydro-2-oxo-1H-imidazo[4,5-b]quinolin-7-yloxy) propyl]-4-(2-ethylbutyl)-1-piperazinecarboxamide dihydrochloride (1.43 g, 44%) mp 230°–263° C.

IR (KBr) 1750, 1640, 1540 cm⁻¹; ¹H NMR (DMSO-d₆) δ 0.76 (6H, t, J=7 Hz, (CH₃)₂), 1.33 (4H, nontuplet, J=7 Hz, (CH₂CH₃)₂), 1.67 (1H, m, NCH₂CH(Et)₂), 1.90 (2H, bs, OCH₂CH₂), 2.89 (4H, bs, N-CH₂), 3.19 (2H, t, J=6 Hz, CO.NH.CH₂), 3.40 (4H, m, N-CH₂+axial CO.N-CH₂), 4.04 (4H, bs, OCH₂+equatorial CO.N-CH₂), 7.14 (1H, dd, J=9 Hz, J'=2 Hz, aryl H ortho to O), 7.41 (1H, d, J=2 Hz, aryl H ortho to O), 7.74 (1H, s, aryl H ortho to CO.NH), 7.84 (1H, d, J=9 Hz, aryl H meta to O), 10.74 (1H, bs, NH), 11.64 (1H, bs, NH); MS m/z 454 (MH+).

Anal. Calcd. for C₂₄H₃₄N₆O₃.2HCl:
C, 54.65; H, 6.88; N, 15.93.
Found: C, 54.97; H, 7.28; N, 15.63.

The compounds of Examples 5, 6 and 7 were prepared by the procedures of Examples 1, 2 and 3.

EXAMPLE 5

Ethyl 3-[(2,3-dihydro-2-oxo-1H-imidazo4,5-b]quinolin-7-yl)oxy]propyl]carbamate (7a)

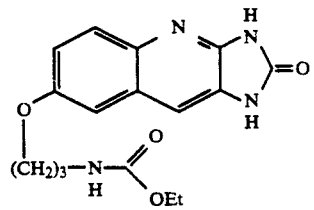

Isolated 1.94 g, mp 269°–270° C. (dec).

IR (KBr) 1725 cm⁻¹; ¹H NMR (DMSO-d₆) δ 1.20 (3H, bs, CH₃), 1.95 (2H, bs, CH₂), 3.25 (2H, bs, NH.CH₂), 3.90 to 4.25 (4H, m, (OCH₂)₂), 7.00 to 7.80 (4H, m, aryl H); ¹³C NMR 14.53, 29.15, 37.28, 59.48, 69.29, 107.01, 109.58, 117.92, 124.38, 126.55, 127.36, 138.32, 145.27, 154. 63, 155.33, 156.23; MS m/z 331 (MH+).

Anal. Calcd. for C₁₆H₁₈N₄O₄.0.15H₂O:
C, 57.70; H, 5.54; N, 16.82; H₂O, 0.81.
Found: C,57.30; H, 5.47; N, 16.76; H₂O, 0.10.

EXAMPLE 6

N-Cyclohexyl-N'-[3-[(2,3-dihydro-2-oxo-1H-imidazo[4,5-b]quinolin-7-yl)oxy]propyl]-N-methylurea (7b)

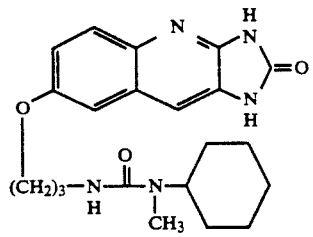

Isolated 2.65 g, mp 210° C. (dec).

IR (KBr) 1720, 1625 cm⁻¹; ¹H NMR (DMSO-d₆) δ 0.90 to 1.85 (10H, m, CH₂), 1.97 (2H, bs, CH₂), 2.68 (3H, s, N'-CH₃), 3.26 (2H, bs, N-CH₂), 3.95 (1H, bs, N-CH), 4.18 (2H, bs, OCH₂), 6.31 (1H, bs, NH), 7.17 (1H,d, J=8 Hz, aryl H ortho to O), 7.32 (1H, s, aryl H ortho to O), 7.53 (1H, s, aryl H ortho to CO.NH), 7.72 (1H, d, J=8Hz, aryl H meta to O); MS m/z 285 (MH+-CH₃NHcC₆H₁₃).

Anal. Calcd. for C₂₁H₂₇N₅O₃.0.25H₂O:
C, 62.75; H, 6.90; N,17.42; H₂O, 1.12.
Found: C, 62.35; H, 6.57; N, 17.47; H₂O, 0.97.

EXAMPLE 7

N-[3-(2,3-dihydro-2-oxo-1H-imidazo[4,5-b]quinolin-7-yl)oxy]propyl]-4-morpholinecarboxamide (7d)

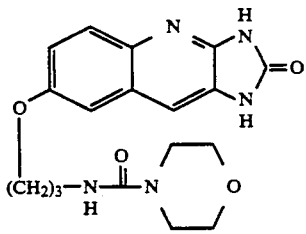

Isolated 3.20 g, mp 258°–262° C.

IR (KBr) 1720, 1625 cm$^{-1}$; $^1$H NMR (DMSO-d$_6$) δ 1.95 (2H, bs, CH$_2$) 3.30 (6H, bs, NH.CH$_2$+N-(CH$_2$)$_2$), 3.62 (4H, bs, O(CH$_2$)$_2$), 4.23 (2H, bs, OCH$_2$), 6.77 (1H, bs, NH), 7.16 (1H, d, J=8 Hz, aryl H ortho to O), 7.38 (1H, s, aryl H ortho to O), 7.57 (1H, s, aryl H ortho to CO.NH), 7.75 (1H, d, J=8 Hz, aryl H meta to O); MS m/z 284 (MH$^+$ -morpholine).

Anal. Calcd. for C$_{18}$H$_{21}$N$_5$O$_4$.0.35H$_2$O:

C, 57.24; H, 5.79; N, 18.54; H$_2$O, 1.67.

Found: C, 57.56; H, 5.68; N, 18.79; H$_2$O, 1.56.

The compounds of Examples 8–26 were prepared by the procedure of Example 4.

EXAMPLE 8

N-[3-(2,3-dihydro-2-oxo-1H-imidazo[4,5-b]quinolin-7yloxy)propyl]-4-(phenylmethyl)-1-piperidinecarboxamide hydrochloride (7e)

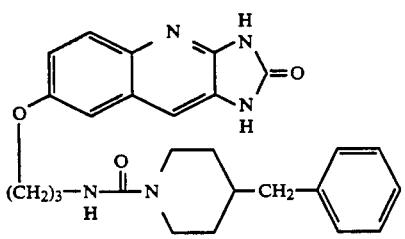

mp 253°–261° C.

IR (KBr) 1750, 1620 cm$^{-1}$; $^1$H NMR (DMSO-d$_6$) δ 0.99 (2H, m, CH$_2$), 1.45 (2H, d, J=13 Hz, CH$_2$), 1.59 (1H, m, CH.CH$_2$Ph), 1.89 (2H, quintet, J=6 Hz, OCH$_2$CH$_2$), 2.42 (2H, d, J=7 Hz, CH$_2$Ph), 2.51 (2H, q, J=13 Hz, axial CO.NCH$_2$), 3.19 (2H, t, J=6 Hz, CO.NH.CH$_2$), 3.90 (2H, d, J=13 Hz, equatorial CO.NCH$_2$), 4.04 (2H, t, J=6 Hz, OCH$_2$), 7.08 to 7.30 (6H, m, aryl H), 7.39 (1H, d, J=2 Hz, aryl H ortho to O), 7.68 (1H, s, aryl H ortho to CO.NH), 7.81 (1H, d, J=9 Hz, aryl H meta to O), 11.42 (1H, s, NH); MS (FAB) m/z 460 (MH$^+$).

Anal. Calcd. for C$_{26}$H$_{29}$N$_5$O$_3$.HCl.0.45H$_2$O:

C, 61.94; H, 6.18; N, 13.89; H$_2$O, 1.63.

Found: C, 61.94; H, 6.10; N, 13.84; H$_2$O, 0.90.

EXAMPLE 9

4-(Cyclohexylmethyl)-N-[3-(2,3-dihydro-2-oxo-1H-imidazo[4,5-b]quinolin-7yloxy)propyl]-1-piperazinecarboxamide dihydrochloride (7f)

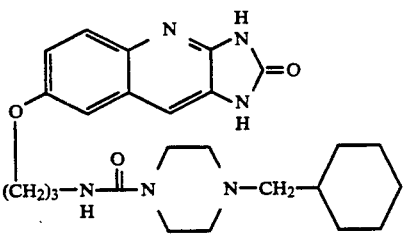

mp 259°–263° C.

IR (KBr) 1730, 1640, 1540 cm$^{-1}$; $^1$H NMR (DMSO-d$_6$) δ 0.90 (2H, m, CH$_2$), 1.14 (3H, m, CH$_2$+CH), 1.45 to 1.83 (6H, m, CH$_2$), 1.92 (2H, t, J=6 Hz, OCH$_2$CH$_2$), 2.85 (4H, bs, N-(CH$_2$)$_2$), 3.21 (2H, t, J=6 Hz, CO.NH.CH$_2$), 3.35 (4H, m, N-CH$_2$+axial CO.N-CH$_2$), 3.95 to 4.10 (4H, m, OCH$_2$ +equatorial CO.N-CH$_2$), 4.22 (2H, bs, H$^+$), 6.96 (1H, bs, NH), 7.14 (1H, dd, J=9 Hz, J'=2 Hz, aryl H ortho to O), 7.32 (1H, d, J=2 Hz, aryl H ortho to O), 7.54 (1H, s, aryl H ortho to CO.NH), 7.68 (1H, d, J=9 Hz, aryl H meta to O), 10.65 (1H, bs, NH), 11.10 (1H, s NH); MS (FAB) m/z 467 (MH$^+$).

Anal. Calcd. for C$_{25}$H$_{34}$N$_6$O$_3$.2HCl.0.47H$_2$O:

C, 54.10; H, 6.62; N, 15.14; H$_2$O, 2.80.

Found: C, 54.10; H, 6.65; N, 14.84; H$_2$O, 1.25.

EXAMPLE 10

4-(Cycloheptylmethyl)-N-[3-(2,3-dihydro-2-oxo-1H-imidazo[4,5-b]quinolin-7yloxy)propyl]-1piperazinecarboxamide dihydrochloride (7g)

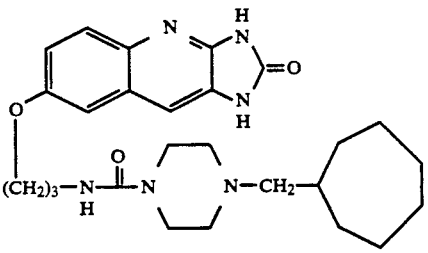

mp 239°–285° C.

IR (KBr) 1750, 1640, 1540 cm$^{-1}$; $^1$H NMR (DMSO-d$_6$) δ 1.00 (2H, m, CH$_2$), 1.10 to 1,70 (10H, m, CH$_2$), 1.72 (1H, m, CH), 1.89 (2H, bs, OCH$_2$CH$_2$), 2.86 (4H, bs, N-(CH$_2$)$_2$), 3.19 (2H, bs, CO.NH.CH$_2$), 3.35 (4H, bs, N-CH$_2$+axial CO.N-CH$_2$), 4.00 (4H, bs, OCH$_2$ +equatorial CO.N-CH$_2$), 7.20 (1H, dd, J=9 Hz, J'=2 Hz, aryl H ortho to O), 7.40 (1H, d, J=2 Hz, aryl H ortho to O), 7.71 (1H, s, aryl H ortho to CO.NH), 7.82 (1H, d, J=9 Hz, aryl H meta to O), 10.64 (1H, bs, NH), 11.56 (1H, s NH); MS m/z 481 (MH$^+$).

Anal. Calcd. for C$_{26}$H$_{36}$N$_6$O$_3$.2HCl.0:

C, 56.41; H, 6.92; N, 15.18.

Found: C, 56.65; H, 7.21; N, 15.21.

EXAMPLE 11

4-(Cyclopentylmethyl)-N-[3-(2,3-dihydro-2-oxo-1H-imidazo[4,5-b]quinolin-7yloxy)propyl]-1-piperazinecarboxamide dihydrochloride (7h)

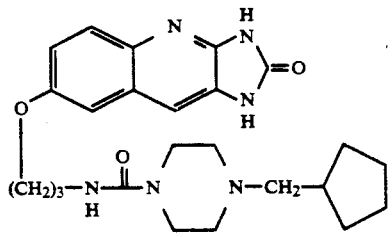

mp 241°-285° C.

IR (KBr) 1750, 1635, 1540 cm$^{-1}$; $^1$H NMR (DMSO-d$_6$) δ 1.10 (2H, m, CH$_2$), 1.30 to 1.55 (4H, m, CH$_2$), 1.73 (2H, m, CH$_2$), 1.89 (2H, bs, OCH$_2$CH$_2$), 2.20 (1H, quintet, J=7 Hz, CH), 2.85 to 3.15 (4H, m, N-(CH$_2$)$_2$), 3.19 (2H, bs, CO.NH.CH$_2$), 3.20 to 3.40 (4H, m, N-CH$_2$+axial CO.N-CH$_2$), 4.02 (4H, bs, OCH$_2$ +equatorial CO.N-CH$_2$), 7.16 (1H, dd, J=9 Hz, J'=2 Hz, aryl H ortho to O), 7.38 (1H, d, J=2 Hz, aryl H ortho to O), 7.74 (1H, s, aryl H ortho to CO.NH), 7.84 (1H, d, J=9 Hz, aryl H meta to O), 10.92 (1H, bs, NH), 11.74 (1H, bs NH); MS (FAB) m/z 453 (MH+).

Anal. Calcd. for C$_{24}$H$_{32}$N$_6$O$_3$.2HCl.0.28H$_2$O:
C, 54.35; H, 6.57; N, 15.84; H$_2$O, 0.93.
Found: C, 54.34; H, 6.63; N, 15.62; H$_2$O, 3.11.

EXAMPLE 12

4-(Cyclohexylethyl)-N-[3-(2,3-dihydro-2-oxo-1H-imidazo[4,5-b]quinolin-7yloxy)propyl]-1-piperazinecarboxamide dihydrochloride (7i)

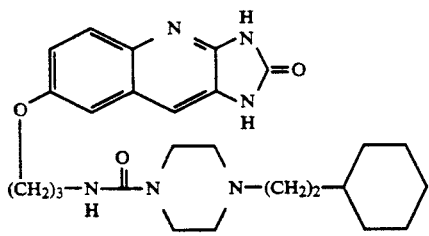

mp 255°-275° C.

IR (KBr) 1750, 1640, 1540 cm$^{-1}$; $^1$H NMR (DMSO-d$_6$) δ 0.82 (2H, m, CH$_2$), 1.08 (4H, m, CH$_2$), 1.58 (7H, m, CH$_2$), 1.91 (2H, t, J=6 Hz, OCH$_2$CH$_2$), 2.84 (2H, m, NCH$_2$), 2.99 (2H, bs, CO.NH.CH$_2$), 3.2 (4H, m, N-CH$_2$), 3.38 (2H, d, J=12 Hz, +axial CO.N-CH$_2$), 4.06 (4H, m, OCH$_2$ +equatorial CO.N-CH$_2$), 7.20 (1H, dd, J=9 Hz, J'=2 Hz, aryl H ortho to O), 7.42 (1H, d, J=2 Hz, aryl H ortho to O), 7.73 (1H, s, aryl H ortho to CO.NH), 7.84 (1H, d, J=9 Hz, aryl H meta to O), 11.27 (1H, bs, NH), 11.57 (1H, s NH); MS (FAB) m/z 481 (MH+).

Anal. Calcd. for C$_{26}$H$_{36}$N$_6$O$_3$.2HCl.0.33H$_2$O:
C, 55.83; H, 6.96; N, 15.02; H$_2$O, 1.05.
Found: C, 55.82; H, 7.11; N, 14.71; H$_2$O, 3.45.

EXAMPLE 13

N-[3-(2,3-dihydro-2-oxo-1H-imidazo[4,5-b]quinolin-7yloxy)propyl -4-(tetrahydro-2H-pyran-2-yl)methyl]-1-piperazinecarboxamide dihydrochloride ethanol solvate (7j)

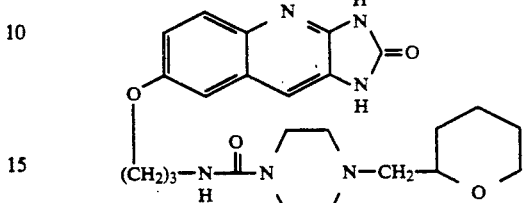

mp 222°-250° C.

IR (KBr) 1750, 1630, 1540 cm$^{-1}$; $^1$H NMR (DMSO-d$_6$) δ 1.02 (1.8H, t, J=7 Hz, CH$_3$CH$_2$OH), 1.14 (1H, t, J=7 Hz, CH$_2$), 1.44 (4H, m, CH$_2$), 1.74 (1H, bs, CH$_2$), 1.91 (2H, t, J=6 Hz, OCH$_2$CH$_2$), 3.00 (2H, m, CO.NH.CH$_2$), 3.00 to 3.32 (4H, m, N-CH$_2$), 3.35 to 3.50 (3H, m, OCH$_2$+axial CO.N-CH$_2$), 3.40 (1.2H, q, J=7 Hz, CH$_3$CH$_2$OH), 3.85 (2H, m, OCH$_2$ of ring), 4.05 (4H, m, OCH$_2$+equatorial CO.N-CH$_2$), 6.01 (2H, bs, H+), 7.18 (1H, dd, J=9 Hz, J'=2 Hz, aryl H ortho to O), 7.38(1H, d, J=2 Hz, aryl H ortho to O), 7.63 (1H, s, aryl H ortho to CO.NH), 7.75 (1H, d, J=9 Hz, aryl H meta to O); MS (FAB) m/z 469 (MH+).

Anal. Calcd. for C$_{24}$H$_{32}$N$_6$O$_4$.2HCl.0.53H$_2$O.0.61C$_2$H$_5$OH:
C, 52.32; H, 6.74; N, 14.52; H$_2$O, 1.64.
Found: C, 52.31; H, 6.83; N, 14.52; H$_2$O, 3.80.

EXAMPLE 14

N-[3-(2,3-dihydro-2-oxo-1H-imidazo[4,5-b]quinolin-7yloxy)propyl]-4-(2-methylpropyl]-1-piperazinecarboxamide dihydrochloride 7k)

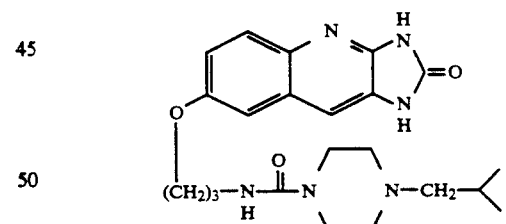

mp 234°-265° C.

IR (KBr) 1750, 1640, 1540 cm$^{-1}$; $^1$H NMR (DMSO-d$_6$) δ 0.86 (6H, t, J=6 Hz, CH(CH$_3$)$_2$), 1.86 (2H, bs, OCH$_2$CH$_2$), 1.99 (1H, septuplet, J=6 Hz, NCH$_2$CH), 2.85 (4H, bs, N-CH$_2$), 3.15 (2H, bs, CO.NH.CH$_2$), 3.25 to 3.50 (4H, m, N-CH$_2$(CH$_3$)$_2$+axial CO.N-CH$_2$), 3.98 (4H, bs, OCH$_2$+equatorial CO.N-CH$_2$), 7.15 (1H, dd, J=9 Hz, J'=2 Hz, aryl H ortho to O), 7.35 (1H, d, J=2 Hz, aryl H ortho to O), 7.73 (1H, s, aryl H ortho to CO.NH), 7.82 (1H, d, J=9 Hz, aryl H meta to O), 10.71 (1H, bs, NH), 11.81 (1H, bs, NH); MS m/z 427 (MH+).

Anal. Calcd. for C$_{22}$H$_{30}$N$_6$O$_4$.2HCl.0.27H$_2$O:
C, 52.40; H, 6.50; N, 16.67; H$_2$O, 0.97.
Found: C, 52.40; H, 6.76; N, 16.31; H$_2$O, 2.35.

EXAMPLE 15

N-[3-(2,3-dihydro-2-oxo-1H-imidazo[4,5-b]quinolin-7yloxy)propyl]-4-(2-propylpentyl)-1-piperazinecarboxamide dihydrochloride (7m)

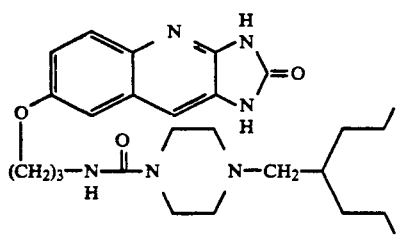

mp 208°-240° C.

IR (KBr) 1750, 1640 cm$^{-1}$; $^1$H NMR (DMSO-d$_6$) δ 0.78 (6H, t, J=7 Hz, (CH$_3$)$_2$), 1.10 to 1.40 (8H, m, CH$_2$), 1.77 (1H, bs, NCH$_2$CH(Pr)$_2$), 1.90 (2H, bs, OCH$_2$CH$_2$), 2.88 (4H, bs, N-CH$_2$), 3.19 (2H, bs, CO.NH.CH$_2$), 3.20 to 3.45 (4H, m, N-CH$_2$+axial CO.N-CH$_2$), 4.02 (4H, bs, OCH$_2$ +equatorial CO.N-CH$_2$), 7.18 (1H, dd, J=9 Hz, J'=2 Hz, aryl H ortho to O), 7.38 (1H, d, J=2 Hz, aryl H ortho to O), 7.70 (1H, s, aryl H ortho to CO.NH), 7.81 (1H, d, J=9 Hz, aryl H meta to O), 10.74 (1H, bs, NH), 11.58 (1H, s, NH); MS m/z 483 (MH+).

Anal. Calcd. for C$_{26}$H$_{38}$N$_6$O$_3$.2HCl:
C, 56.21; H, 7.26; N, 15.13.
Found: C, 56.40; H, 7.51; N, 15.01.

EXAMPLE 16

N-[3-(2.3-dihydro-2-oxo-1H-imidazo4.5-b]quinolin-7yloxy)propyl]-1-piperazinecarboxamide dihydrochloride ethanol solvate (7n)

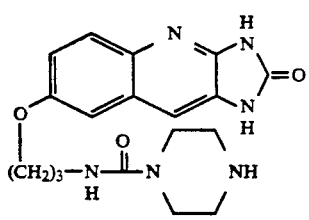

mp 274°-285° C.

IR (KBr) 1740, 1640, 1540 cm$^{-1}$; $^1$H NMR (DMSO-d$_6$) δ 1.03 (t, J=7 Hz, CH$_3$CH$_2$OH), 1.91 (2H, t, J=6 Hz, OCH$_2$CH$_2$), 2.99 (4H, bs, N-CH$_2$), 3.21 (2H, t, J=6 Hz, CO.NH.CH$_2$), 3.32 (1H, bs, CO.N-CH$_2$), 3.54 (3H, m, CO.N-CH$_2$), 4.06 (2H, t, J=6 Hz, OCH$_2$), 7.18 (1H, dd, J=9 Hz, J'=2 Hz, aryl H ortho to O), 7.37 (1H, d, J=2 Hz, aryl H ortho to O), 7.64 (1H, s, aryl H ortho to CO.NH), 7.76 (1H, d, J=9 Hz, aryl H meta to O), 9.47 (1H, bs, NH), 11.31 (1H, s, NH); MS m/z 371 (MH+).

Anal. Calcd. for C$_{18}$H$_{22}$N$_6$O$_3$.2HCl.0.5C$_2$H$_5$OH:
C, 48.93; H, 5.84; N, 18.02.
Found: C, 49.34; H, 5.68; N, 18.12.

EXAMPLE 17

N-[3-(2,3-dihydro-2-oxo-1H-imidazo[4,5-b]quinolin-7yloxy)propyl]-4-(phenylmethyl)-1-piperazinecarboxamide dihydrochloride ethanol solvate (7o)

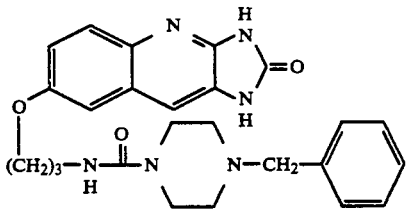

mp 224°-239° C.

IR (KBr) 1750, 1620, 1550 cm$^{-1}$; $^1$H NMR (DMSO-d$_6$) δ 1.03 (3H, t, J=7 Hz, CH$_3$CH$_2$OH), 1.91 (2H, quintet, J=6 Hz, OCH$_2$CH$_2$), 2.88 (2H, m, CO.NH.CH$_2$), 3.10 to 3.30 (6H, m, N-CH$_2$+axial CO.NCH$_2$), 3.41 (2H, q, J=7 Hz, CH$_3$CH$_2$OH), 4.06 (4H, m, OCH$_2$+equatorial CO.NCH$_2$), 4.28 (2H, d, J=5 Hz, NCH$_2$Ph), 7.19 (1H, dd, J=9 Hz, J'=2 Hz, aryl H ortho to O), 7.35 to 7.45 (4H, m, aryl H), 7.60 (2H, m, aryl H), 7.63 (1H, s, aryl H ortho to CO.NH), 7.76 (1H, d, J=9 Hz, aryl H meta to O), 11.29 (1H, s, NH), 11.60 (1H, bs, NH); MS (FAB) m/z 461 (MH+).

Anal. Calcd. for C$_{25}$H$_{28}$N$_6$O$_3$.2HCl.0.5H$_2$O.C$_2$H$_5$OH:
C, 55.10; H, 6.34; N, 14.25; H$_2$O, 1.53.
Found: C, 55.39; H, 6.29; N, 14.07; H$_2$O, 1.18.

EXAMPLE 18

N-[3-(2,3-dihydro-2-oxo-1H-imidazo[4,5-b]quinolin-7yloxy)propyl]-4-(4-chlorophenyl)methyl)-1-piperazine carboxamide dihydrochloride (7p)

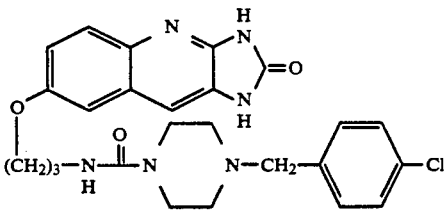

mp 256°-268° C.

IR (KBr) 1750, 1630, 1540 cm$^{-1}$; $^1$H NMR (DMSO-d$_6$) δ 1.90 (2H, t, J=6 Hz, OCH$_2$CH$_2$), 2.88 (2H, m, CO.NH.CH$_2$), 3.21 (6H, bs, N-CH$_2$+axial CO.NCH$_2$), 4.00 to 4.15 (4H, m, OCH$_2$+equatorial CO.NCH$_2$), 4.28 (2H, d, J=4 Hz, NCH$_2$Ar), 6.55 (bs, H$_2$O), 7.17 (1H, dd, J=9 Hz, J'=2 Hz, aryl H ortho to O), 7.35 (1H, d, J=2 Hz, aryl H ortho to O), 7.64 (2H, d, J=8 Hz, aryl H meta to Cl), 7.60 (1H, s, aryl H ortho to CO.NH), 7.49 (2H, d, J=8 Hz, aryl H ortho to Cl), 7.72 (1H, d, J=9 Hz, aryl H meta to O), 11.20 (1H, s, NH), 11.60 (1H, bs, NH); MS (FAB) m/z 495 (MH+).

Anal. Calcd. for C$_{25}$H$_{27}$N$_6$O$_3$Cl.2HCl.H$_2$O:
C, 51.25; H, 5.33; N, 14.34; H$_2$O, 3.05.
Found: C, 51.47; H, 5.20; N, 13.94; H$_2$O, 3.62.

EXAMPLE 19

N-[3-(2,3-dihydro-2-oxo-1H-imidazo[4,5-b]quinolin-7yloxy)propyl]-4-[(4-fluorophenyl)methyl]-1-piperazine carboxamide dihydrochloride ethanol solvate (7g)

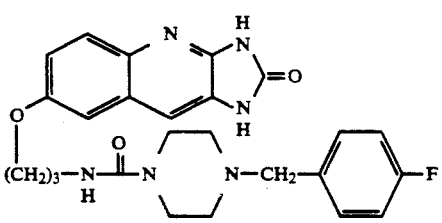

mp 240°-265° C.

IR (KBr) 1750, 1630, 1540 cm$^{-1}$; $^1$H NMR (DMSO-d$_6$) δ 1.02 (3H, t, J=7 Hz, CH$_3$CH$_2$OH), 1.91 (2H, t, J=6 Hz, OCH$_2$CH$_2$), 2.88 (2H, m, CO.NH.CH$_2$), 3.10 to 3.35 (6H, m, N-CH$_2$+axial CO.NCH$_2$), 3.40 (2H, q, J=7 Hz, CH$_3$CH$_2$OH), 4.05 (4H, m, OCH$_2$+equatorial CO.NCH$_2$), 4.29 (2H, d J=4 Hz, NCH$_2$Ar), 7.15 to 7.30 (3H, m, aryl H), 7.40 (1H, d, J=2 Hz, aryl H ortho to O), 7.68 (3H, m, aryl H), 7.49 (2H, d, J=8 Hz, aryl H ortho to Cl), 7.80 (1H, d, J=9 Hz, aryl H meta to O), 11.42 (1H, s, NH), 11.70 (1H, s, NH); MS (FAB) m/z 479 (MH+)

Anal. Calcd. for C$_{25}$H$_{27}$N$_6$O$_3$F.2HCl.0.5H$_2$O.C$_2$H$_5$OH:

C, 53.50; H, 5.78; N, 14.26; H$_2$O, 1.54.

Found: C, 53.50; H, 5.81; N, 14.28; H$_2$O, 2.34.

EXAMPLE 20

N-[3-(2,3-dihydro-2-oxo-1H-imidazo[4,5-b]quinolin-7yloxy)propyl]-4-[(2-phenylethyl)-1-piperazinecarboxamide dihydrochloride (7r)

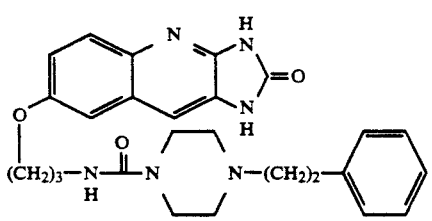

mp 217°-235° C.

IR (KBr) 1750, 1630, 1540 cm$^{-1}$; $^1$H NMR (DMSO-d$_6$) δ 1.92 (2H, t, J=6 Hz, OCH$_2$CH$_2$), 2.94 (2H, m, CO.NH.CH$_2$), 3.06 (2H, m, CH$_2$Ph), 3.22 (6H, m, N-CH$_2$), 3.50 (2H, d, J=12 Hz, axial CO.NCH$_2$), 4.10 (4H, m, OCH$_2$+equatorial CO.NCH$_2$), 5.33 (1H, bs, exchangeable H), 7.10 to 7.45 (7H, m, aryl H), 7.65 (1H, s, aryl H ortho to CO.NH), 7.78 (1H, d, J=9 Hz, aryl H meta to O), 11.32 (1H, s, NH), 11.48 (1H, bs, NH); MS (FAB) m/z 475 (MH+).

Anal. Calcd. for C$_{26}$H$_{30}$N$_6$O$_3$.2HCl.0.93H$_2$O:

C, 55.35; H, 6.05; N, 14.90; H$_2$O, 3.03.

Found: C, 55.35; H, 6.06; N, 14.86; H$_2$O, 2.97.

EXAMPLE 21

N-[3-(2,3-dihydro-2-oxo-1H-imidazo[4,5-b]quinolin-7yloxy)propyl]-4-[(2-thienyl)methyl]-1-piperazinecarboxamide dihydrochloride ethanol solvate (7s)

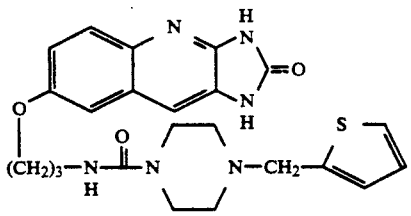

mp 246°-272° C.

IR (KBr) 1750, 1630, 1540 cm$^{-1}$; $^1$H NMR (DMSO-d$_6$) δ 1.04 (2H, t, J=7 Hz, CH$_3$CH$_2$OH), 1.91 (2H, quintet, J=6 Hz, OCH$_2$CH$_2$), 2.87 (2H, m, CO.NH.CH$_2$), 3.10 to 3.45 (6H, m, N-CH$_2$+axial CO.NCH$_2$), 3.41 (1.3H, q, J=7 Hz, CH$_3$CH$_2$OH), 4.06 (4H, m, OCH$_2$+equatorial CO.NCH$_2$), 4.52 (2H, bs, NCH$_2$Th), 6.94 (2H, bs, exchangeable H), 7.10 (1H, dd, J=5 Hz, J'=3 Hz, thienyl-4H), 7.18 (1H, dd, J=9 Hz, J'=2 Hz, aryl H ortho to O), 7.38 (1H, d, J=2 Hz, aryl H ortho to O), 7.40 (1H, d, J=3 Hz, thienyl, H), 7.63 (1H, s, aryl H ortho to CO.NH), 7.66 (1H, d, J=5 Hz, thienyl H), 7.75 (1H, d, J=9 Hz, aryl H meta to O), 11.27 (1H, s, NH), 11.67 (1H, bs, NH); MS (FAB) m/z 467 (MH+).

Anal. Calcd. for C$_{23}$H$_{26}$N$_6$O$_3$S.2HCl.0.25H$_2$O.0.64C$_2$H$_5$OH:

C, 50.86; H, 5.68; N, 14.66; H$_2$O, 2.77.

Found: C, 50.86; H, 5.61; N, 14.66; H$_2$O, 0.77.

EXAMPLE 22

N-3-(2,3-dihydro-2-oxo-1H-imidazo[4,5-b]quinolin-7yloxy)propyl]-4-[(3-thienyl)methyl]-1-piperazinecarboxamide dihydrochloride (7t)

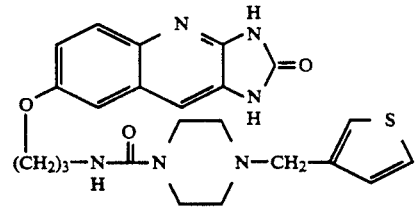

mp 273°-285° C.

IR (KBr) 1750, 1635, 1540 cm$^{-1}$; $^1$H NMR (DMSO-d$_6$) δ 1.91 (2H, quintet, J=6 Hz, OCH$_2$CH$_2$), 2.86 (2H, m, CO.NH.CH$_2$), 3.05 to 3.30 (6H, m, N-CH$_2$+axial CO.NCH$_2$), 4.05 (4H, m, OCH$_2$+equatorial CO.NCH$_2$), 4.28 (2H, d, J=4.5 Hz, NCH$_2$Th), 7.19 (1H, dd, J=9 Hz, J'=2 Hz, aryl H ortho to O), 7.39 (1H, d, J=2 Hz, aryl H ortho to O), 7.61 (1H, dd, J=5 Hz, J'=3 Hz, thienyl H), 7.66 (1H, s, aryl H ortho to CO.NH), 7.77 (1H, s, thienyl H), 7.78 (1H, d, J=9 Hz, aryl H meta to O), 11.36 (1H, s, NH), 11.70 (1H, s, NH); MS (FAB) m/z 467 (MH+).

Anal. Calcd. for C$_{23}$H$_{26}$N$_6$O$_3$S.2HCl.0.17H$_2$O:

C, 50.92; H, 5.27; N, 15.49; H$_2$O, 0.57.

Found: C, 50.92; H, 5.60; N, 15.27; H$_2$O, 2.30.

EXAMPLE 23

N-[3-(2,3-dihydro-2-oxo-1H-imidazo[4,5-b]quinolin-7yloxy)propyl]-4-(1-piperidinyl)-1-piperidinecarboxamide dihydrochloride (7u)

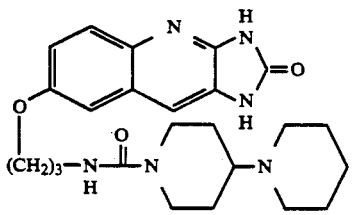

mp 298°-301° C.

IR (KBr) 1750, 1630, 1540 cm$^{-1}$; $^1$H NMR (DMSO-d$_6$) δ 1.20 to 2.10 (12H, m, CH$_2$), 2.61 (2H, t, J=12 Hz, axial N-CH$_2$), 2.81 (2H, m, CO.NH.CH$_2$), 3.10 to 3.40 (5H, m, N-CH+N-CH$_2$+axial CO.NCH$_2$), 4.05 (4H, m, OCH$_2$+equatorial CO.NCH$_2$), 7.19 (1H, dd, J=9 Hz, J'=2 Hz, aryl H ortho to O), 7.41 (1H, d, J=2 Hz, aryl H ortho to O), 7.67 (1H, s, aryl H ortho to CO.NH), 7.78 (1H, d, J=9 Hz, aryl H meta to O), 10.78 (1H, bs, NH), 11.39 (1H, s, NH); MS (FAB) m/z 453 (MH+).

Anal. Calcd. for C$_{24}$H$_{32}$N$_6$O$_3$.2HCl.0.1H$_2$O:
C, 54.66; H, 6.54; N, 15.94; H$_2$O, 0.34.
Found: C, 54.66; H, 6.50; N, 15.53; H$_2$O, 4.39.

EXAMPLE 24

N-[3-(2,3-dihydro-2-oxo-1H-imidazo[4,5-b]quinolin-7yloxy)propyl]-4-(2-pyrimidinyl)-1-piperazinecarboxamide dihydrochloride (7v)

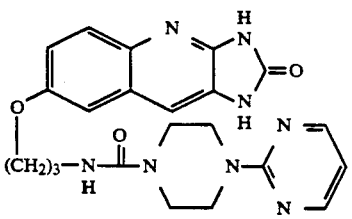

mp 236°-269° C.

IR (KBr) 1750, 1625, 1535 cm$^{-1}$; $^1$H NMR (DMSO-d$_6$) δ 1.92 (2H, quintet, J=6 Hz, OCH$_2$CH$_2$), 3.23 (2H, t, J=6 Hz, CO.NH.CH$_2$), 3.40 (4H, m, N-CH$_2$), 4.07 (2H, t, J=6 Hz, OCH$_2$), 6.73 (1H, t, J=5 Hz, pyrimidinyl H), 7.19 (1H, dd, J=9 Hz, J'=2 Hz, aryl H ortho to O), 7.38 (1H, d, J=2 Hz, aryl H ortho to O), 7.63 (1H, s, aryl H ortho to CO.NH), 7.76 (1H, d, J=9 Hz, aryl H meta to O), 8.43 (2H, d, J=5 Hz, pyrimidinyl H), 11.26 (1H, s, NH); MS (FAB) m/z 449 (MH+).

Anal. Calcd. for C$_{22}$H$_{24}$N$_8$O$_3$.2HCl.0.45H$_2$O:
C, 49.90; H, 5.12; N, 21.16; H$_2$O, 1.57.
Found: C, 49.91; H, 5.11; N, 20.85; H$_2$O, 1.53.

EXAMPLE 25

N-[3-(2,3-dihydro-2-oxo-1H-imidazo[4,5-b]quinolin-7yloxy)propyl]-4-(2-pyridyl)-1-piperazinecarboxamide dihydrochloride ethanol solvate (7w)

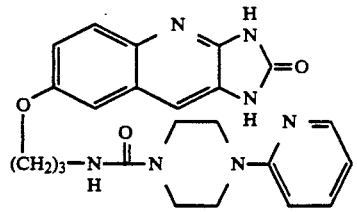

mp 256°-270° C.

IR (KBr) 1740, 1630, 1540 cm$^{-1}$; $^1$H NMR (DMSO-d$_6$) δ 1.06 (t, J=7 Hz, CH$_3$CH$_2$OH), 1.92 (2H, m, OCH$_2$CH$_2$), 3.23 (2H, m, CO.NH.CH$_2$), 3.35 (q, J=7 Hz, CH$_3$CH$_2$OH), 3.50 (4H, bs, N-CH$_2$), 4.06 (2H, m, OCH$_2$), 4.27 (2H, bs, exchangeable H), 6.94 (1H, bs, aryl H), 7.14 (1H, d, J=8 Hz, aryl H ortho to O), 7.25 to 7.45 (2H, m, aryl H), 7.55 (1H, s, aryl H ortho to CO.NH), 7.69 (1H, d, J=8 Hz, aryl H meta to O), 7.99 (2H, bs, pyridyl H), 11.11 (1H, bs, NH); MS (FAB) m/z 448 (MH+).

Anal. Calcd. for C$_{23}$H$_{25}$N$_7$O$_3$.2HCl.0.45H$_2$O.0.5C$_2$H$_5$OH:
C, 52.26; H, 5.65; N, 17.78.
Found: C, 52.25; H, 5.34; N, 17.75.

What is claimed is:

1. A compound of the formula

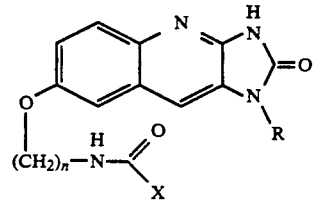

wherein
R is H, or C$_1$-C$_4$ lower alkyl;
X is OR$^1$, NR$^2$R$^3$, or

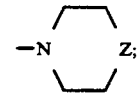

Z is O, NH, N(CH$_2$)$_m$R$^5$ or CHR$^6$;
R$^1$ is C$_1$-C$_4$ lower alkyl;
R$^2$ is H, or C$_1$-C$_4$ lower alkyl;
R$^3$ is H, C$_1$-C$_4$ lower alkyl, or C$_4$-C$_8$ cycloalkyl;
R$^5$ is C$_1$-C$_8$ alkyl, C$_4$-C$_8$ cycloalkyl, 2-pyranyl, 2-thienyl, 3-thienyl, piperidinyl-N-CH, N-2-pyridyl, N-2-pyrimidinyl, or substitued or unsubstituted phenyl wherein the substituent is halogen;
R$^6$ is H, 1-piperidinyl, or phenylmethyl;
m is an integer of 1-3; and
n is an integer of 1-5;
or pharmaceutically acceptable salt thereof.

2. The compound of claim 1 which is N-[3-(2,3-dihydro-2-oxo-1H-imidazo[4,5-b]quinolin-7yloxy)propyl]-4-(2-ethylbutyl)-i-piperazinecarboxamide or pharmaceutically acceptable salt thereof.

3. The compound of claim 1 which is N-[3-(2,3-dihydro-2-oxo-1H-imidazo[4,5-b]quinolin-7yloxy)propyl]-4-(phenylmethyl)-1-piperidinecarboxamide or pharmaceutically acceptable salt thereof.

4. The compound of claim i which is 4-(cyclohexylmethyl)-N-[3-(2,3-dihydro-2-oxo-1H-imidazo[4,5-b]quinolin-7yloxy)propyl]-1-piperazinecarboxamide or pharmaceutically acceptable salt thereof.

5. The compound of claim I which is 4-(cycloheptylmethyl)-N-[3-(2,3-dihydro-2-oxo-1H-imidazo[4,5-b]quinolin-7yloxy)propyl]-1-piperazine-carboxamide or pharmaceutically acceptable salt thereof.

6. The compound of claim i which is 4-(cyclopentylmethyl)-N-[3-(2,3-dihydro-2-oxo-1H-imidazo[4,5-b]quinolin-7yloxy)propyl]-1-piperazine-carboxamide or pharmaceutically acceptable salt thereof.

7. The compound of claim 1 which is 4-(cyclohexylethyl)-N-[3-(2,3-dihydro-2-oxo-1H-imidazo [4,5-b]quinolin-7yloxy)propyl]-1-piperazinecarboxamide or pharmaceutically acceptable salt thereof.

8. The compound of claim 1 which is N-[3-(2,3-dihydro-2-oxo-1H-imidazo[4,5-b]quinolin-7yloxy) propyl]-4-[(tetrahydro-2H-pyran-2-yl)methyl]-1-piperazinecarboxamide or pharmaceutically acceptable salt thereof.

9. The compound of claim 1 which is N-[3-(2,3-dihydro-2-oxo-1H-imidazo[4,5-b]quinolin- 7yloxy)propyl]-4-(2-methylpropyl)-1-piperazinecarboxamide or pharmaceutically acceptable salt thereof.

10. The compound of claim I which is N-[3-(2,3-dihydro-2-oxo-1H-imidazo[4,5-b]quinolin-7yloxy) propyl]-4-(2-propylpentyl)-1-piperazinecarboxamide or pharmaceutically acceptable salt thereof.

11. The compound of claim 1 which is N-[3-(2,3-dihydro-2-oxo-1H-imidazo[4,5-b]quinolin-7yloxy) propyl]-1-piperazinecarboxamide or pharmaceutically acceptable salt thereof.

12. The compound of claim 1 which is N-[3-(2,3-dihydro-2-oxo-1H-imidazo[4,5-b]quinolin-7yloxy) propyl]-4-(phenylmethyl)-1-piperazine-carboxamide or pharmaceutically acceptable salt thereof.

13. The compound of claim 1 which is N-[3-(2,3-dihydro-2-oxo-1H-imidazo[4,5-b]quinolin-7yloxy) propyl]-4-[(4-chlorophenyl)methyl]-1-piperazinecarboxamide or pharmaceutically acceptable salt thereof.

14. The compound of claim i which is N-[3-(2,3-dihydro-2-oxo-1H-imidazo[4,5-b]quinolin-7yloxy) propyl]-4-[(4-fluorophenyl)methyl]-1-piperazinecarboxamide or pharmaceutically acceptable salt thereof.

15. The compound of claim 1 which is N-[3-(2,3-dihydro-2-oxo-1H-imidazo[4,5-b]quinolin-7yloxy) propyl]-4-(2-phenylethyl)-1-piperazinecarboxamide or pharmaceutically acceptable salt thereof.

16. The compound of claim 1 which is N-[3-(2,3-dihydro-2-oxo-1H-imidazo[4,5-b]quinolin-7yloxy) propyl]-4-[(2-thienyl)methyl]-1-piperazinecarboxamide or pharmaceutically acceptable salt thereof.

17. The compound of claim 1 which is N-[3-(2,3-dihydro-2-oxo-1H-imidazo[4,5-b]quinolin-7yloxy) propyl]-4-[(3-thienyl)methyl]-1-piperazine-carboxamide or pharmaceutically acceptable salt thereof.

18. The compound of claim 1 which is N-[3-(2,3-dihydro-2-oxo-1H-imidazo[4,5-b]quinolin-7yloxy) propyl]-4-(1-piperidinyl)-1-piperidinecarboxamide or pharmaceutically acceptable salt thereof.

19. The compound of claim 1 which is N-[3-(2,3-dihydro-2-oxo-1H-imidazo[4,5-b]quinolin-7yloxy) propyl]-4-(2-pyrimidinyl)-1-piperazine-carboxamide or pharmaceutically acceptable salt thereof.

20. The compound of claim 1 which is N-[3-(2,3-dihydro-2-oxo-1H-imidazo[4,5-b]quinolin-7yloxy) propyl]-4-(2-pyridyl)-1-piperazinecarboxamide or pharmaceutically acceptable salt thereof.

21. A method for inhibiting blood platelet aggregation in a mammal which comprises administering a therapeutically effective amount of a compound of claim 1 or a pharmaceutically acceptable salt thereof.

22. The pharmaceutical composition which comprises a therapeutically effective amount of a compound of claim 1 or a pharmaceutically acceptable acid addition salt thereof and a pharmaceutical carrier.

* * * * *

UNITED STATES PATENT AND TRADEMARK OFFICE
CERTIFICATE OF CORRECTION

PATENT NO. : 5,196,428

DATED : March 23, 1993

INVENTOR(S): Nicholas A. Meanwell

It is certified that errors appear in the above-identified patent and that said Letters Patent is hereby corrected as shown below:

Title page, item [54]
Cover page, in the title please delete "QINOLINYL" and insert --QUINOLINYL--.

Title page, col. 2,
Cover page, please insert attorney name --Michelle A. Kaye--.

Column 24, Claim 2, line 67, after "(2-ethylbutyl)-" please delete "i" and insert --1--.

Column 25, Claim 4, line 5, after "claim" please delete "i" and insert --1--.

Column 25, Claim 5, line 9, after "claim" please delete "I" and insert --1--.

Column 25, Claim 6, line 13, after "claim" please delete "i" and insert --1--.

Column 25, Claim 10, line 30, after "claim" please delete "I" and insert --1--.

Column 26, Claim 14, line 5, after "claim" please delete "i" and insert --1--.

Signed and Sealed this

Thirtieth Day of November, 1993

Attest:

BRUCE LEHMAN

Attesting Officer

Commissioner of Patents and Trademarks